United States Patent [19]

Mandal et al.

[11] Patent Number: 5,846,748
[45] Date of Patent: Dec. 8, 1998

[54] METHOD FOR DIAGNOSING VISCERAL LEISHMANIASIS IN A PATIENT BY IDENTIFICATION OF A NEW KEY MARKER NAMELY 9-O-ACETYLATED SIALOGLYCOCONJUGATE

[75] Inventors: Chitra Mandal; Vineeta Sharma; Mitali Chatterjee, all of Calcutta, India

[73] Assignee: The Council of Scientific & Industrial Research, New Delhi, India

[21] Appl. No.: 824,171

[22] Filed: Mar. 26, 1997

[30] Foreign Application Priority Data

Nov. 15, 1996 [IN] India .............................. 2502/DEL/96

[51] Int. Cl.$^6$ ..................................... G01N 33/53
[52] U.S. Cl. .................. 435/7.22; 435/7.25; 435/7.92; 436/501; 436/520; 436/811; 436/827
[58] Field of Search ................... 435/7.22, 7.25, 435/7.92; 436/501, 520, 811, 827

[56] References Cited

U.S. PATENT DOCUMENTS 5,411,865  5/1995  Reed ........................................ 435/7.22

OTHER PUBLICATIONS

Palatnik–de–Sousa et al., "Leishmania donovani: titration of antibodies to the fucose–mannose ligand as an aid in diagnosis and prognois of visceral leishmaniasis," Trans. Royal Soc. Trop. Med. Hyg. 89: 390–393 1995.

Sen et al., "The specificity of the binding site of Achatinin$_H$, a sialie acid–binding lectin from *Achatina fulica*," Carbohydr. Res. 268: 115–125 1995.

*Primary Examiner*—Carol A. Spiegel
*Attorney, Agent, or Firm*—John P. White; Cooper & Dunham LLP

[57] ABSTRACT

This invention relates to identification of a new key marker namely 9-O-Acetylated sialoglycoconjugate with the help of a known 9-O acetylsialic acid binding lectin, Achatinin-H useful for the diagnosis of visceral leishmaniasis, by a rapid, accurate haemagglutination assay.

16 Claims, No Drawings

METHOD FOR DIAGNOSING VISCERAL LEISHMANIASIS IN A PATIENT BY IDENTIFICATION OF A NEW KEY MARKER NAMELY 9-O-ACETYLATED SIALOGLYCOCONJUGATE

FIELD OF THE INVENTION

The present invention relates to a simple and effective method of diagnosing Visceral leishmaniasis (VL). More specifically, the invention is for identification of a new key marker namely 9-O-Acetylated sialoglycoconjugate with the help of a known 9-O acetylsialic acid binding lectin, Achatinin-H useful for the diagnosis of visceral leishmaniasis (VL), by a rapid, accurate haemagglutination assay.

BACKGROUND AND PRIOR ART REFERENCES OF THE INVENTION

Leishmania is a member of the trypanosomatid protozoa and is the causative agent of leishmaniasis. Leishmaniasis comprises a spectrum of diseases that are widely distributed in tropical and subtropical countries ranging in severity from self healing lesions to severely mutilating muco-cutaneous involvement or visceral infections (kala-azar).

The leishmania parasite has a digenetic life cycle: (a) an intracellular, non motile, small and ovoid shaped amastigotes that multiply within the macrophages of the susceptible vertebrate host and (b) an extracellular, flagellated, motile, slender and spindle shaped promastigotes which replicate in the digestive tract of the invertebrate vector Phlebotome insect (sandfly) (Chang K. P., Fong D. and Bray R. S., Leishmaniasis (1985) Chang and Bray eds. Elseviers Science Publishers).

About 20 million people worldwide, are reported to be victims of various forms of leishmaniasis and about 400,00 new cases appear every year. Leishmaniasis is endemic in the tropical regions of South and Central America, Africa, the Mediterranean Basin, the Middle East and the Indian subcontinent. The population at risk totals 350 million and DALYS (disability adjusted life years) lost are estimated at 2,060,000 (WHO. The Leishmaniases. Report of a WHO expert committee. WHO Tech. Rep.Ser. 1984:701). Three million individuals suffer from various forms of leishmaniasis and the number of new cases each year being 1.5 millions of which 500,000 are visceral leishmaniasis. These estimates take into account poor reporting from rural areas and the lack of obligatory reporting in many endemic areas.

Based on the clinical patterns of disease caused by different species, the leishmaniasis may be classified into three groups (1) Cutaneous leishmaniasis is the most prevalent, producing skin ulcers which spontaneously heal (2) Mucocutaneous leishmaniasis, which initially causes lesions which may heal but reappear causing mutilating severely disfiguring lesions and (3) Visceral leishmaniasis, a systemic disease which is nearly always fatal if left untreated.

Visceral leishmaniasis causes large scale epidemics and an epidemic situation has been reported from the Indian subcontinent in 1991-91 owing to a four year interruption of DDT spraying as also in North-eastern and Southern Sudan owing to war and cumulative risk factors. It is estimated that VL may have killed 75,000 people during this period (Modabber F. 1987; The Leishmaniases Pearce J. M. and Pearce A. M. eds. Tropical Disease research, TDR eighth program report).

Kala-azar has been known to exist in India since long. On the basis of available records, the disease is more than a century old. The first recorded which can be ascribed to kala-azar was in 1824 in Mohammedpore (Jessore District) now Bangladesh. Records of epidemics of kala-azar have been reported in 1885,1897,193,1925 and 1944 showing a mean inter-epidemic period of 10–20 years (Dye C and Wolpert D. M. Trans.R. Soc.Trop. Med.Hyg. (1988),82, 843–850. Visceral leishmaniasis (VL) is presently endemic in eastern parts of India (WHO Technical report series no: 701,1984). The first epidemic in eastern Bihar occurred in 1882 and after a gap of about 10 years the epidemic again occurred in 1891, 1917 and 1933. In 1939, the number of cases reached the colossal figure of 91,822. Thereafter, a declining trend was noticed towards 1939–1940. In 1933, 21 districts of Bihar were badly affected and 9 districts partially affected with a targeted risk population 71.4 million (Status paper on kala-azar in Bihar, Sept. 1993). The most recent and caused outbreaks in Bihar from 1977 to 1992 were estimated to have claimed the lives of thousands and caused severe morbidity of millions more, resulting in severe economic loss. Data available from 1977 to 19990 indicated a total of 332,150 kala-azar patients including 6373 fatal cases (Thakur C. P. and Kumar. Ann. Trop.Med. and Parasitol 1992: 86; 355–359).

Visceral leishmaniasis can also present as a coinfection in conjunction with AIDS as leishmania may survive in immunologically incompetent hosts. AIDS destroys immunological competence and permits parasite multiplication. There has been a dramatic increase in the overlapping of the two diseases; more particularly in Asia where the numbers have increases from 30,000 in 1992 to 250,000 in 1993. In Bombay, sex workers many of whom are Nepalese frequently become infected by AIDS and then return to Nepal where VL is endemic (Lower plains of Terai).

Overlapping of the two diseases is also increasing sharply in the Western hemisphere. Data indicate that certain areas (Southern France, parts of Spain, Portugal and Italy ) the incidence of Leishmaniasis in AIDS patients can reach 2–3% (Modabber; The Leishmaniases. Pearce J. M. and Pearce A. M. eds. Tropical Disease research (1987); TDR eighth program report. It is estimated that tin Southern Europe between 25 and 70% of adult VL cases are related to AIDS and 1.5 to 9% of AIDS Cases suffer from newly acquired or related VL (Report of the consultative meeting on Leishmania/HIV infection, Rome, September 1994; WHO Leisb/95.35)

In such cases of VL and AIDS coinfection, the individual will be immunocompromised and the currently available immunological methods of diagnosis which are dependent on the circulating antileishmanial antibody titre may provide a false negative result. Only the Polymerase chain Reaction (PCR) can be applied for diagnosis of leishmaniasis in such patients. It is therefore relevant to develop newer modes of diagnosis keeping the immunocomprised patient in mind.

A significant problem in the clinical diagnosis of active VL is that the clinical features including fever, cough, diarrhoea, weight loss and enlarged liver and spleen may resemble those of several other infections and other lymphoproliferative disorders (Rees P. H. and Kager P. A. (1987) The leishmaniases of Biology and Medicine New York N.Y.: Academic press vol.2, pp d 583–616). Several infectious diseases including malaria, typhoid, schistosomiasis and Chagas disease have geographical distributions that may overlap those of VL. These factors, as well as serological cross reactivity may confound the diagnostic procedure. For decades, the definitive diagnosis of kala azar is still based on invasive procedures to directly demonstrate the parasite in tissue i.e. spleen, bone marrow, lymph node and skin, unfortunately the insensitivity of the procedure, inconvenience and its potential risks many patients of VL are empirically treated for coendemic diseases like tuberculosis, malaria etc. (Adhya S., Chatterjee M., Hassan M. Q. et al.1995 trans. R. Soc. Trop.Med.Hyg.89; 622–624. In addition, the method does not identify the species of parasite which is particularly important in the differential diagnosis of cutaneous and mucocutaneous leishmaniasis. Other presently available methods of diagnosis of VL are principally immunological based test namely:

1. Direct agglutination test: Described first by Allen and Kagan (Am.J.Trop.Med.Hyg. 1975: 24; 232–236 ) the direct agglutination test (DAT) has since been notified for the serodiagnosis of VL by Harith et al. (Trans.R. Soc.Trop.Med .Hyg.1986: 80; 583–587). Based on their visible agglutination of formalin fixed promastigotes by circulating antibodies from VL patient sera, the test is simple, specific, economical, all of which are relevant factors for applicability in underdeveloped countries. The principal disadvantage of this test are (1) The agglutination titre of cured patients can remain high upto eight years following recovery (Hailu, Trans.R.Trop.Med.Hyg. 1990: 84; 673) and (2) instability of the antigen precludes its widespread usage in field studies.

2. Test Indirect Fluorescent Antibody(IFAT): In this method, washed formalin or acetone fixed promastigotes are used as antigen for detecting circulating antibodies in VL by an immunoperoxidase method (Duxbury R. E. and Sudan E. H. Am.J. Trop.Med.Hyg. 1964: 13; 525–529; Shaw J. J. and Voller A. Trans.R. Soc. Trop. Med.Hyg. 1964: 59; 535–544). The principal drawbacks are (i) cross reactivity with patients of trypanosorniasis and pulmonary tuberculosis have been reported (Camargo M. E. and Robonato C. Am.J. Trop. Med.Hyg. 1969; 18; 500 ) and (ii) facilities of a fluorescent microscope are few and far between.

3. Enzyme linked immunosorbent assay(ELISA): Using promastigote lysates as the coating antigen on microtitre plates, circulating antibodies in patient sera can be detected by the immunuoperoxidase method. ELISA has been widely used for the diagnosis of VL as the technique is simple, sensitive and specific and widely applicable in developing countries (Ho M., Leewenberg J., Mbugua G., Warnachi A. and Voller A. Am. J. Trop. Med.Hyg. 1983: 32; 943–946; Jahn A and Diesfield H. J. Trans. R,Soc, Trop.Med.Hyg.1983: 77; 451–454; Decock K. M., Hodgen A. N., Channon J. Y., Arap Siongok T. K., Lucas S. B. and Rees P. H. J. Inf. Dis. 1985:151; 750–752).

Presently, patents filed in the area of diagnosis of visceral leishmaniasis focus immunological methods of diagnosis namely:

1. An in vitro culture of partic stages of tissue parasites-an axenic media, free of serum and macromolecules, of controlled pH and osmolarity, also derived polypeptides, antibodies and nucleic acids useful for diagnosis, vaccination and drug screening (Lemesre J. A. and Lemesre J; WPI Acc no: 95-006795/01.

2. Leishmania antigen compsn-containing fucose-mannose ligand cell fractions (Borojevic R., Palatnik de souza C. B., wPI Acc no:95-067600/10).

3. New differentially expressed Leishmania genes and proteins used to develop prods for vaccination against and diagnosis of Leishmania infection. Charest H. and Matlashewshi G., WPI Acc no: 95-162100/22.

4. Isolated differentially expressed genes of Leishmania—useful as vaccines diagnostic reagents and for generation of immunological reagents. Charest H. and Matlashewski G.; WPI Acc no: 95-115445/15.

5. Diagnosis of visceral leishmaniasis in dogs or human includes admin. of leishmania thermal shock protein, etc. Peas de Andrade C.R. and Paes de Andrade P. WPI Acc no: 94-303433/38.

6. Diagnosis of leishmaniasis—by determining the presence of antibodies that bind to a K39 repeat unit antigen Reed S. and Reed S. G., WPI Acc no 94-249402/30.

7. Preparation of immunoassays for detection of antigens or inhibitors in secretions or extracts—using inhibitors or antigens with specific affinity, adsorbed on solid carriers Scharestein J.; WPI Acc no: 93-227725/29.

8. Non cross reacting Leishmania antigens-used for diagnosis of visceral leishmaniasis avoiding false positive results. Berneman A. and Rolland X.; WPI Acc no: 89-061181/06.

9. Native fractions isolated from Leishmania- with immunogenic, lymphoproliferative and interleukin realizing activities useful e.g. in vaccines and diagnosis. Berneman A., Burger L., Dubois C., Dubois P., Leclerc C., Cavallion J. M. and Rolland X.; WPI Acc no: 89-010082/02.

10. Monoclonal antibodies to leishmania antigens useful for diagnosis and purification of new immunogenic antigens. Inst. Pasteur. WPI Acc no: 86-106661/16.

11. Recovery of parasite protective antigenic factors useful in vaccines esp. against malaria and as diagnostic agents. Dantonio L. E.; WPI Acc no: 83-758892/36.

12. Hybridoma clones producing monoclonal factors leishmania antibodies useful as immunoassay diagnostic reagents and therapeutically. David J. R. and Pratt D.; WPI Acc no: 83-53932k/22.

Like all immunological tests, the main drawbacks of ELISA assay are (i) firstly, inability to distinguish between present and past infection. Its use is therefore limited to initial diagnosis of the disease, and it can not assess clinical cure or predict relapse and (ii) secondly, in immunocompromised individuals the possibility of false negative results exists In the context of increasing incidences of combined VL and AIDS confection this is a major disadvantage.

Modifications of the basic ELISA have been carried out e.g. DOT-ELISA (Pappas M. G., Hajkowski R. and Hockmeyer W. T. Am. J. Trop.Med.Hyg. 1983 64; 205–214; Badaro R., Reed S. G., Barral A., Orge G. and Jones T. C. Am.J.Trop.Med. Hyg.1986: 35; 72–78) and use of species specific monoclonal antibodies.(Jaffe C. l., Bennett E., Grimaldi G. Jr. and McMahon Pratt D. J. Immunol. 1984: 133; 440–447; Jaffe C. L. and McMahon Pratt D. Trans. R. Soc. Trop. Med.Hyg.1987: 81; 587–594).

4. DNA BASED PROBES: Development of a diagnostic test based on the polymerase chain reaction (PCR) where selective amplification of DNA has allowed detection of minute traces of parasites DNA (Hasan M. Q., Ghosh A., Ghosh S. S., Gupta M., Basu D., Mallik D. and Adhya S. J. Parasitol. 1993 107; 509–517: DNA encoding an immunodominant fragment of haemoflagellate protozoa; Powell C. WPI Acc No: 95-392925/50; DNA probe specific for Leishmania donovani complex—used for detection, diagnosis and monitoring of leishmania infection (Miles M. A., Howard M. K. and Kelly J. M., WPI Acc no:91-096019/14). The PCR method however has a few relevant drawbacks in terms of its widespread usage in India namely: (1) Requirement of sophisticated instruments (2) DNA extraction is an extended, tedious process and (3) the process therefore needs technical expertise to avoid the possibility of false positivity due to DNA contamination. Therefore, such a sophisticated method is not applicable for diagnosis of kala-azar, which is a predominantly rural disease, where laboratory facilities available are minimal.

5. Another approach adopted is detection and quantification of non viral infections (Bacterial, parasitic, fungal and mycoplasma) by measuring complex formed with beta 2-glycoprotein I. (Graafland H., Rucheton M. and Stefas E., WPI Acc No:96-118692/13). However, it is a non specific marker of infection.

Sialic acids are a family of derivatives of N-acetyl or N-glycolyl neuraminic acids and are very important constituents of cell surface architecture. Sialic acids play an important role in receptors for viruses, peptide hormones and toxins (Rosenberg A. and Schengrund C. L. Plenum Press, N.Y. 1976). Sialic acids also function as masking agents or antigens, receptors and other recognition sites of the cell surface (Burness A. T. H. Animal viruses, Chapman and Hall, N.Y. 1981: 63–84). The O substituted sialic acids exhibit species and tissue specific distribution in animals (Schauer R. adv. Carbohydr. Chem. Biochem. 1982: 40; 131–234)>Changes in sialic acid and the degree of O-acetylation of sialic acid residues have been reported in transformed and malignant cells.

Detection of sialic acids residues can be approached through the use of sialic acid specific lectins found in a variety of invertebrates (Mandal C. and Mandal C. Experientia 1990: 46; 433–441; Yeaton R. W. Dev.Comp.Immun.1981: 5; 391–402) and serum (Tsai C. M., Zopf D. A., Yu R. K., Wister R. Jr. Ginsberg V. Proc.Natl. Acad.Sci. USA 1977: 74; 4591–4594).

Achatinin-H is a sialic acid binding lectin which binds preferentially to sialic acid derivatives which are: (a) O-acetylated at the C-9 position of the parent molecule and (b) have an $\alpha$ 2, 6 linkage (Mandal C. and Basu S. Boichem. Biophys Res Comm 1987; 148: 795–810, Sen G., Chowdhary M. and Mandal C. Carbohydrate Research 1995, 268: 115–125).

Sialic acid residues are commonly O-acetylated at the C-4, 7 and 9 position of the parent molecule. Of these, 9-O-acetylation occurs in very small amounts in normal small amounts in normal lymphocytes and importantly this 9-O-acetylated sialoglycoconjugate is absent in eiythrocytes.(Schauer R Adv. Carbohydr. Chem.Biochem. 1982: 40; 131–234). Accordingly, we have exploited the selective binding of Achatinin-H to 9-O-acetylated derivatives (9-O-AcSG) to serve as a diagnostic tool for detecting specific cell surface transformations involving the biomarker. It has allowed us to identify the presence of 9-O-AcSG on the erythrocytes of patients suffering from visceral leishmaniasis. The presence of 9-O-AcSG has been corroborated by fluorometric quantitative analysis of 9-O-acetylated sialic acid on the surface of erythrocytes.

Furthermore, this key marker namely 9-O-AcSG has been found to be present only during the stage of parasitosis i.e. when the leishmania parasite is circulating. Following effective antileishmanial therapy; the haemagglutination titre becomes negative. Therefore, this process can also state the parasitolgical status of the patient.

Considering the drawbacks of the above mentioned methods, development of a diagnostic assay which is simple, sensitive and specific is urgently required to control leishmaniasis related sufferings.

OBJECTS OF THE INVENTION

The main objective of the present invention is to provide a simple and effective method of diagnosing visceral leishmaniasis by a rapid and accurate haemagglutination assay.

Another objective of the invention is for a process for the identification of a new key marker namely 9-O-acetylated sialoglycoconjugate with the help of a known 9-O-acetylsialic acid binding lectin, Achatinin-H useful for the diagnosis of visceral leishmaniasis, by a rapid, accurate haemaglutination assay.

SUMMARY OF THE INVENTION

To meet the above objects, the present invention relates to identification of a new key marker namely 9-O-Acetylated sialoglycoconjugate with the help of a known 9-O acetylsialic acid binding lectin, Achatinin-H useful for the diagnosis of visceral leishmaniasis, by a rapid, accurate haemagglutination assay.

DETAILED DESCRIPTION OF THE INVENTION

Accordingly, the present invention provides a method of diagnosing Visceral leishmaniasis by the identification of a new key marker namely 9-O-Acetylated sialoglycoconjugate with the help of a known 9-O-acetylsialic acid binding lectin, Achatinin-H useful for the diagnosis of visceral leishmaniasis, by a rapid and accurate haemaglutination assay, which method comprises:

(a) collection and processing of blood in presence of anticoagulant from patients suspected to be suffering from visceral leishmaniasis, (b) erythrocytes is washed with an isotonic balanced salt solution and erythrocyte suspension was prepared, (c) binding of erythrocytes with different concentrations of the 9-0-acetyl sialic acid binding lectin Achatinin-H in the presence of calcium is carried out in 96 well U bottom microtitre plates at room temperature, (d) determining the haemagglutination titre, and (e) correlating the result with the status of the disease as assessed.

In a preferred embodiment of the invention, following are the possible permutations and combinations of the above mentioned process.

Whole heparinised blood is used for erythrocytes separation. Alsevers solution or any anticoagulant can be used for collection of blood. The concentration of Achatinin-H can vary in the range of 2.0–3.0 $\mu$g. 0.85% saline is used as the reaction mixture. Other buffers such as Tris hydrochloride buffer can also be used. 96 well U bottom microtitre plates can also be used for haemagglutination of erythrocytes. 96 well V shaped microtitre plates can also be used. Tarson (indigenous) or Nunc or Costar or corning plates are equally good. Small glass or plastic tubes also can be used; since the starting volume would be greater here its uneconomical. The incubated 0.25 ml for haem- agglutination of erythrocytes. The incubated can be varied from 0.2–0.5 ml for visible agglutination. Erylirocytes have been incubated at 25°–35° C. in presence of Achatinin-H. The temperature can be varied from 4° C. to room temperature. Whole reaction was carried out in presence of 30 mM of $Ca^{2+}$. However, the concentration of $Ca^{2+}$ can be varied from 25 to 30 mM. The reaction time of 30–60 minutes was used for maximum agglutination. The time may be extended to 120 minutes for incubations carried out at 4° C. The titre did not change even if the plate was kept at 4° C. in the refrigerator overnight 2% erythrocytes suspension/well gave best visible haemagglutination. 1% erythrocytes suspension/well can also be used 2–3 days old (stored at 10° C.) blood can be used. However, a reduction in the titre was observed. Agglutination titre was determined by the naked eye. Microscopic agglutination can also be assessed by examination of erythrocytes using an ordinary light microscope.

The following examples are given by way of illustration of the present invention and should not be construed to limit the scope of the present invention.

Example 1

0.50 ml of blood was collected in heparin from patients (n=20) suffering from visceral leishmaniasis, as confirmed by direct demonstration of the leishmania parasite in giemsa stained splenic or bone marrow material. In parallel, then possibility of cross reactivity was checked by conducting the haemagglutination assay with erythrocytes of patients suffering from malaria (n=5), tuberculosis (n=5) and normal individuals from endemic (n=10) and non-endemic areas (n=10). a randomly selected group of VL patients (n=10) were assessed by the assay following completion of their 21 day course of sodium stibogluconate. Their bone marrow examination revealed to leishmania parasites at the end of their antileishmanial treatment. For the Haemagglutination Assay (HA), a 9-O-acetylated sialic acid binding lectin, Achatinin-H was purified (Basu S., Sarkar M. and Mandal C. Cell Biochem 1986; 71: 149–57) and stored at 4° C. Using 96 well U-bottomed plates, 25 $\mu$l of AchatininH(50 $\mu$g/ml) was added to the first well and serial 1:1 dilution carried out in the subsequent 9 well. To this, 25 $\mu$l of 0.1M CaCl$_2$ and 25 $\mu$l of 2% erythrocyte suspension was added. Titres of haemagglutination were scored by visual assessment after 60 min. of incubation at 25° C. The reciprocal of the highest dilution of Achatinin-H that produced visible agglutination was taken as the end point haemagglutination titre. The titre remained positive 48–72 hours following collection of blood which was stored in the refrigerator.

Example 2

0.50 ml of blood was collected in heparinised tubes from patients (n=25) suffering from visceral leishmaniasis as confirmed by direct demonstration of the leishmania parasite in giemsa stained splenic or bone marrow material. In parallel, the possibility of cross reactivity was checked by conducting the haemagglutination assay with erythrocytes of patients suffering from malaria (n=5), tuberculosis (n=5) and normal individuals from endemic and non-endemic areas (n=10). A randomly selected group of VL patients "(n=10)" were assessed by HA following completion of their 21 day course of sodium stibogluconate. Their bone marrow examination revealed no leishmania parasites at the end of their antileishmanial treatment. For the Haemagglutination assay (HA), a 9-O-acetylated sialic acid binding lectin, Achatinin-H was purified (Basu S., Sarkar Mandal C.Mol Cell Biochem 1986; 71: 149–57) and stored at 4° C. Using 96 well U-bottomed plates, 25 $\mu$l of Achatinin-H (100 $\mu$g/ml) was added to the first well and serial 1:1 dilution carried out in the subsequent 9 wells. To this, 25 $\mu$l of 0.1M CaCl$_2$ and 25 $\mu$l of 2% erythrocyte suspension was added. Titres of haemagglutination were scored by visual assessment after 30 min. of incubation at 30° C. The reciprocal of the highest dilution of Achatnin-H that produced visible agglutination was taken as the end point haemagglutination remained. The titre positive 48–72 hours following collection of blood which was stored in the refrigerator.

Example 3

0.50 ml of blood was collected in heparinised tubes from patients (n=15) suffering from visceral leishmaniasis as confirmed by direct demonstration of the leishmania parasite in giemsa stained splenic or bone marrow material. In parallel, the possibility of cross reactivity was checked by conducting the haemagglutination assay with erythrocytes of patients suffering from malaria (n=5), tuberculosis (n=5) and normal individuals form endemic (n=10) and non endemic(n=10 areas). A randomly selected group of VL patients (n=10) were assessed by HA following completion of their 21 day course of sodium stibogluconate. Their bone marrow examination revealed no leishmania parasites at the end of their antileishmanial treatment. For the Haemagglutination assay (HA), a 9-O-acetylated sialic acid binding lectin,. AchatininH was purified (Basu S, Sarkar M and Mandal C.Mol Cell Biochem 1986; 71: 149–57). using 96 well U-bottomed plates 25, $\mu$l of Achatinin-H (400 $\mu$g/ml) was added to the first well and serial 1:1 dilution carried out in the subsequent 9 wells. To this, 25 $\mu$l of 0.1M CaCl$_2$ 25 $\mu$l of 2% erythrocyte suspension was added. Titres of haemagglutination were scored by visual assessment after 60 min. of incubation at 4°–10° C. The reciprocal of the highest dilution of Achatinin-H that produced visible agglutination was taken as the titre. The titre remained positive 48–72 hours following collection of blood which was stored in the refrigerator.

Example 4

0.50 ml of blood was collected in heparinised tubes from patients (n=20) suffering from visceral leishmaniasis, as confirmed by direct demonstration of the leishmania parasite in giemsa stained splenic or bone marrow material. In parallel, the possibility of cross reactivity was checked by conducting the haemagglutination assay with erythrocytes of patients suffering from malaria(n=5), tuberculosis (n=5) and normal individuals from endemic (n=10) and non endemic areas (n=10). A randomly selected group of VL parasites VL patients (n=10) were assessed by HA following completion of their 21 day course of sodium stibogluconate. Their bone marrow examination revealed no leishmania parasites at the end of their antileishmanial treatment. For the Haemagglutination assay (HA), 9-O-acetylated sialic acid binding lectin; Achatinin-H was purified (Basu S., Sarkar M. and Mandal C. Mol. Cell Biochem 1986 71:149–57). Using 96 well U-bottomed plates, (50 $\mu$g/ml) was added to the first well and serial 1:1 dilution carried out in the subsequent 9 wells. To this, 25 $\mu$l of 0.2M CaCl$_2$ and 25 $\mu$l of 4% eithrocyte suspension was added. Titres of haemagglutination were scored by visual assessment after overnight incubation at 4°–10° C. The reciprocal of the highest dilution of AchatininH that produced visible agglutination was taken as the titre. The titre remained positive 48–72 hours following collection of blood which was stored in the refrigerator.

The haemagglutination assay carried out according to the process of the present invention (examples 1–4) has been identified as an accurate method for diagnosis of visceral leishmaniasis and has the following properties:

| Categories | No: | Age Range (years) | M:F | Spleen size (cm) Average Range | HA (x ± SEM) |
|---|---|---|---|---|---|
| VL a. Pre treatment | 85 | 2.5–55.0 | 52:23 | 5.7 1–13.0 | 142.7 ± 44.7 |
| b. Post- | 40 | 4.0–55.0 | 21:19 | 1.8 1–4.5 | — |

-continued

| Categories | No: | Age Range (years) | M:F | Spleen size (cm) Average | Range | HA (x ± SEM) |
|---|---|---|---|---|---|---|
| treatment | | | | | | |
| Malaria | 20 | 10.0–60.0 | 12:8 | 1.2 | 0–3.0 | — |
| Tuberculosis | 20 | 7.0–60.0 | 13:7 | 1.4 | 0–4.0 | — |
| Controls | 40 | 4.0–50.0 | 25:15 | — | — | — |
| a. endemic areas | | | | | | |
| b. nonendemic areas | 40 | 25.0–35.0 | 21:19 | — | — | — |

RESULTS

1. Patients diagnosed as visceral leishmaniasis (n=85) gave a haemaglutination titre ranging from 4 to 1024 units (Table 1). The average haemaglutination titre was 142.7 units. This therefore clearly indicates that this haemagglutination assay can identify patients of visceral leishmaniasis.

2. A randomly selected group (n=40 ) were followed up following a 21 day course of sodium stibogluconate. The haemagglutination titre was negative in all the selected patients. Clinically, they were diagnosed as cured i.e. the leishmania parasite was absent as evidenced by giemsa stained biopsy smears. This indicates that the haemagglutination assay can not only diagnose visceral leishmaniasis, it can also assess whether the patient has been cured following a course of antileishmanial treatment.

Presently available immunological methods used for the diagnosis of VL have a major drawback in their ability to distinguish between present and past infection. Their use is therefore limited to initial diagnosis of the disease and they cannot assess clinical cure or predict relapse. Therefore, the haemagglutination assay is a far superior method as it can assess clinical cure and therefore is able to distinguish between presence and absence of circulating leishmania parasite.

3. No cross reactivity was observed in patients suffering from malaria (n=20) and tuberculosis(n=20) as the haemagglutination titre was negative in these cases. (specificity 100%). In the control groups, both from endemic (n=40) and non-endemic (n=40), individuals of blood groups A,B and O were studied, the haemagglutination titre was negative reconfirming the absence of 9-O-Acetylated sialoglycoconjugates on human erythrocytes. Thus HA had no false positives in all the control groups.

4. The presence of the biomarker, 9-O-AcSG has also been quantified by flurometric analysis of the amount 9-O-acetylated sialic acid present on the erythrocytes (personal communication, data not shown). Our experiments have therefore demonstrated:

(a) Identification of "9-O-acetylated sialoglycoconjugates" i.e. 9-O-AcSG on the surface of erythrocytes of Indian visceral leishmaniasis patients.

(b) The absence of the above mentioned biomarker in patients followed up following a course of antileishmanial treatment. It therefore directly correlates with presence or absence of the leishmania parasite i.e. the Haemagglutination Assay is positive when the parasite is circulating and negative when the parasite has been eliminated by effective chemotherapy. The HA is therefore of diagnostic and prognostic value.

(c) The assay shows no cross reactivity with patients suffering from malaria (n=20) and tuberculosis(n=20) as the haemagglutination titre was negative in these cases. (specificity 100%). In the control groups, both from endemic (n=40) and non-endemic (n=40), individuals of blood groups A,B and O were studied, the haemagglutination titre was negative reconfirming the absence of 9-O-Acetylated sialoglycoconjugates on human etythrocytes. Thus HA had no false positives in all the control groups.

The main advantages of the present invention are:

1. The haemagglutination assay is a simple, sensitive and specific assay for diagnosis of visceral leishmaniasis which can detect the key marker (9-O-AcSG) on the surface of erythrocytes in the acute phase of the disease.

2. It can distinguish between presence and absence of circulating leishmania parasite as agglutination is positive when the parasite is present and negative once the parasite has been eliminated by effective antileishmanial therapy. It can therefore distinguish between the pre- treatment and post-treatment status of the affected individual. It therefore can detect the extent to which the patient has responded to chemotherapy. It therefore indirectly serves as a reflection of the current parasitological status of the patient.

3. The haemagglutination assay is independent of the circulating antileishmanial antibody titre and therefore the results are independent of the individuals immune status.

4. The haemagglutination assay is a simple, and rapid method, easy to perform; blood derived from a finger prick is adequate and requires minimal processing. Multiple samples can be assessed simultaneously and no sophisticated equipment is required. Results can visually analysed and interpretation is very clear cut. Results can be obtained with 60 min and it therefore may be applied in outpatient departments of hospital.

5. The natural abundance of Achatinin H, its long thermal stability for>2 years at 6° C.–10° C. filter sterilised, at a concentration of 1 mg/ml are very relevant factors for field studies.

6. Due to inexpensiveness of the HA (costs Rs 8–10 per sample ), it can be widely applied in developing countries like the Indian subcontinent and Sudan where the disease is widely prevalent. The method is an effective tool for epidemiological studies and merits clinical consideration.

Other applications of the lectin:

The lectin Achatinin-H, is a unique probe for identification of the cell surface marker "9-O-Acetylated sialoglycoconjugate". It has been utilised in two completely different systems, the common feature being the cell surface marker "9-O-Acetylated sialoglycoconjugate". The two diseases in question are (i) visceral leishmaniasis and (ii) acute lymphoblastic leukemia.

Clinically, the two disease processes are completely different from each other and are easily distinguishable as also the mode of treatment are totally different. With regard to the invention the important differences are as follows:

1. In the proposed invention the diagnosis of visceral leishmaniasis is based on the presence of the biomarker "9-O-Acetylated sialoglycoconjugate" on erythrocytes whereas in acute lymphoblastic leukemia it is based on the presence of the biomarker "9-O-Acetylated sialoglycoconjugate" on peripheral blood mononuclear cells.

2. In the proposed invention the diagnosis of visceral leishmaniasis is based on the agglutination of erythrocytes using the lectin Achatinin-H whereas in acute lymphoblastic leukemia it is based on the lymphoproliferative assay using the lectin Achatinin-H.

3. The diagnosis of visceral leishmaniasis is based on the naked eye evaluation of agglutination of erythrocytes using the lectin Achatinin-H whereas in acute lymphoblastic leukemia it is based on the lymphoproliferative assay using the lectin Achatinin-H which is measured either by radiometric or colorometric assay.

4. The haemagglutination assay is positive only during the acute phase of the disease in visceral leishmaniasis prior to treatment whereas in acute lymphoblastic leukemia the detection of minimal residual disease and prediction of relapse the proposed invention is of utmost importance after initial phase of chemotherapy.

We claim:

1. A hemaglutination method for diagnosing and assessing acute visceral leishmaniasis in a patient suspected of suffering from said visceral leishmiasis, which method comprises:
   a. collecting an anticoagulated blood sample from said patient;
   b. separating erythrocytes from said anticoagulated blood sample and preparing an erythrocyte suspension by washing and resuspending said separated erythrocytes in an isotonic balanced salt solution;
   c. providing serial dilutions of a known initial concentration of Achatinin-H which specifically binds 9-O-acetylsialic acid;
   d. reacting each dilution with an equal sized aliquot of said erythrocyte suspension at a temperature from 4°–35° C. in the presence of calcium ions for a time sufficient for said Achatinin-H to bind to and thereby agglutinate any erythrocytes having said 9-O-acetylsialic acid on their surfaces; and
   e. determining a hemagglutination titer by taking the reciprocal of the highest serial dilution that produced a visible agglutination wherein positive hemagglutination indicates a positive diagnosis of said acute visceral leishmaniasis and said titer indicates the level of circulating leishmania parasites.

2. The method as claimed in claim 1 wherein said anticoagulated blood is collected in heparin or Alsever's solution.

3. The method as claimed in claim 1 wherein step c. comprises serially diluting said initial concentration of Achatinin-H 1:1 with said isotonic balanced salt solution.

4. The method as claimed in claim 1 wherein said Achatinin-H in the reaction volumes of step d. is in a range between 2–3 µg.

5. The method as claimed in claim 1 wherein said isotonic salt balanced solution is 0.85% saline.

6. The method as claimed in claim 1 wherein said isotonic salt solution is a Tris-HCl buffered isotonic salt solution.

7. The method as claimed in claim 1 wherein steps c.–e. are performed in a 96 well microtiter plate.

8. The method as claimed in claim 7 wherein step d. comprises reacting a 1–2% erythrocyte suspension in each well.

9. The method as claimed in claim 1 wherein the temperature in step d. ranges from 25°–35° C.

10. The method as claimed in claim 1 wherein the reaction volumes of step d. varies between 0.2–0.5 ml.

11. The method as claimed in claim 1 wherein said calcium ions are present in a concentration from 25 to 30 mM.

12. The method as claimed in claim 1 wherein said reaction time of step d. is 30–120 minutes.

13. The method as claimed in claim 1 wherein said anticoagulated blood sample is up to 2–3 days old and has been stored at 10° C.

14. The method as claimed in claim 1 wherein said visible agglutination is determined by the naked eye.

15. The method as claimed in claim 1 wherein said visible agglutination is assessed a light microscope.

16. The method as claimed in claim 1, further comprising testing multiple anticoagulated blood samples from said patient over time wherein a persistent titer over time correlates to persistence or relapse of said acute visceral leishmaniasis.

* * * * *